United States Patent
Dai et al.

(10) Patent No.: US 8,597,282 B2
(45) Date of Patent: Dec. 3, 2013

(54) DATABASE SYSTEM FOR CENTRALIZED CLINICAL AND RESEARCH APPLICATIONS WITH DATA FROM WAVEFRONT ABERROMETERS

(75) Inventors: Guangming Dai, Fremont, CA (US); Kingman Yee, San Jose, CA (US); Dimitri Chernyak, Santa Clara, CA (US)

(73) Assignee: AMO Manufacturing USA, LLC, Santa Ana, CA (US)

( * ) Notice: Subject to any disclaimer, the term of this patent is extended or adjusted under 35 U.S.C. 154(b) by 1746 days.

(21) Appl. No.: 11/332,824

(22) Filed: Jan. 12, 2006

(65) Prior Publication Data

US 2006/0173644 A1    Aug. 3, 2006

Related U.S. Application Data

(60) Provisional application No. 60/644,227, filed on Jan. 13, 2005.

(51) Int. Cl.
*A61F 9/008* (2006.01)

(52) U.S. Cl.
USPC .................................. 606/5; 606/10

(58) Field of Classification Search
USPC ........ 606/10–13, 5; 607/88–90; 351/221, 206
See application file for complete search history.

(56) References Cited

U.S. PATENT DOCUMENTS

| | | | |
|---|---|---|---|
| 4,669,466 A * | 6/1987 | L'Esperance | 606/3 |
| 5,764,341 A * | 6/1998 | Fujieda et al. | 351/221 |
| 6,572,230 B2 * | 6/2003 | Levine | 351/221 |
| 6,682,196 B2 | 1/2004 | Sheets, Jr. et al. | |
| 6,698,889 B2 | 3/2004 | Pettit et al. | |
| 2003/0151720 A1* | 8/2003 | Chernyak et al. | 351/206 |

FOREIGN PATENT DOCUMENTS

EP          1327948        7/2003

OTHER PUBLICATIONS

Martinez et al; "Effect of Pupillary Dilation on Corneal Optical Aberrations After Photorefractive Keratectomy"; Arch Ophthalmol.; V 116; 1998; pp. 1053-1062.*

* cited by examiner

*Primary Examiner* — David Shay
(74) *Attorney, Agent, or Firm* — AMO Manufacturing USA, LLC.

(57) ABSTRACT

Computer systems, programs, and methods can advantageously be used to process optical data. These approaches often involve modifying a first format data to a second format data, and are useful in simplifying the complications due to data from different wavefront systems, different aberrometer devices and aberrometer software versions, different clinical studies and different measurement conditions. A centralized database system can be used effectively in a clinical research setting, which can be a medical center, a college, or a research department in a company, or in other diagnosis or treatment facilities.

21 Claims, 9 Drawing Sheets

| DATA LOADER | | | | | | |
|---|---|---|---|---|---|---|
| FILE CONNECT EXECUTION HELP | | | | | | |

| CONNECTION | | N | LAST NAME | FIRST NAME | PATIENT ID | EYE | DATE | TIME |
|---|---|---|---|---|---|---|---|---|
| USER NAME: RDLOADER | | 1 | DOE | JOHN | 123456-7 | OD | 2/21/2003 | 09:12 |
| PASSWORD: XXXXXXXX | | 2 | DOE | JOHN | 123456-7 | OD | 2/21/2003 | 09:13 |
| CONNECT | | 3 | DOE | JOHN | 123456-7 | OD | 2/21/2003 | 09:15 |
| | | 4 | DOE | JOHN | 123456-7 | OS | 2/21/2003 | 09:42 |
| STATISTICS | | 5 | DOE | JOHN | 123456-7 | OS | 2/21/2003 | 09:44 |
| ☑ WAVEFRONT DATA | | 6 | DOE | JOHN | 123456-7 | OS | 2/21/2003 | 09:46 |
| VERSION: 3.1 | | 7 | DOE | JOHN | 123456-7 | OD | 3/20/2003 | 16:20 |
| PATIENTS: 256 | | 8 | DOE | JOHN | 123456-7 | OD | 3/20/2003 | 16:21 |
| EYES: 312 | | 9 | DOE | JOHN | 123456-7 | OD | 3/20/2003 | 16:22 |
| RECORDS: 8372 | | 10 | DOE | JOHN | 123456-7 | OS | 3/20/2003 | 16:33 |
| | | 11 | DOE | JOHN | 123456-7 | OS | 3/20/2003 | 16:34 |
| LOAD | | 12 | DOE | JANE | 123456-7 | OS | 3/20/2003 | 16:35 |
| | | 13 | DOE | JANE | W32-88888 | OD | 3/25/2003 | 10:06 |
| | | 14 | DOE | JANE | W32-88888 | OD | 3/25/2003 | 10:08 |
| | | 15 | DOE | JANE | W32-88888 | OD | 3/25/2003 | 10:11 |
| | | 16 | DOE | JANE | W32-88888 | OD | 3/25/2003 | 10:13 |
| | | 17 | DOE | JANE | W32-88888 | OD | 3/25/2003 | 10:15 |
| | | 18 | SMITH | TIM | 12-123456 | OS | 3/26/2003 | 09:21 |

IMPORTED C:\CLINICAL\WAVEFRONT\PC123.DBM

CONNECTED.

DATABASE SYSTEM FOR CENTRALIZED CLINICAL AND RESEARCH APPLICATIONS WITH DATA FROM WAVEFRONT ABERROMETERS

CROSS-REFERENCES TO RELATED APPLICATIONS

This application claims the benefit under 35 USC §119(e) of U.S. Provisional Patent Application No. 60/644,227 filed on Jan. 13, 2005, the full disclosure of which is incorporated herein by reference.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK.

Not Applicable

BACKGROUND OF THE INVENTION

This invention generally relates to laser eye surgery, and in particular, provides methods, devices, and systems for selectively ablating corneal tissue to improve the vision of patients having corneal irregularities.

Laser eye surgery systems and methods are now used to correct defects in vision using a technique known as ablative photodecomposition. In general, these techniques selectively expose the cornea to laser radiation so as to selectively remove and resculpt the cornea and achieve a desired change in shape of the cornea to treat an optical defect. The advent of laser eye surgery has improved ophthalmological treatment for many patients by mitigating or eliminating the need for glasses or contact lenses.

Many patients suffer from optical defects which are not easily treated using known spherical or cylindrical ablation techniques, and wavefront diagnostic approaches have proved to be useful in determining customized corrective ablation shapes for such patients. In fact, by combining laser eye surgical techniques with wavefront diagnostic approaches, it is often possible to achieve visual acuity measurements of 20/20 or better in treated patients.

The combination of photoablative procedures and wavefront diagnostics can present certain difficulties, as such systems are designed by a variety of manufacturers using different platforms. Accordingly, there exists a broad spectrum of data types and formats for wavefront-based laser surgery treatment. To address some of these issues, the Optical Society of America (OSA) has set forth standards for wavefront data. Although such standards are beneficial, the inventors of the present invention have recognized that this standard does not resolve the issues presented by the historically fractious growth of this technology.

In light of the above, it would be desirable to provide improved laser eye surgery devices, systems, and methods. At least some of these objectives are satisfied by the techniques describe below.

BRIEF SUMMARY OF THE INVENTION

A database system can be constructed to centralize clinically available data, including preoperative and postoperative clinical measurements, wavefront data from aberrometers, topography data, optical coherence tomography data, pachymetry data, and the like. For example, there exists a large body of historical or legacy optical data that does not conform with a standard such as the OSA format. The present techniques are suitable for processing such data, as it can be useful for developing or refining optical treatments. In particular, systems according to the present invention can be useful for correlating legacy or historical wavefront data with clinical results to develop therapeutic custom laser ablation shapes. Relatedly, techniques according to the present invention can facilitate the usage of clinical and medical data across different systems or different memory or database implementations. These approaches can also facilitate access and usage of information independently of the systems from which they are generated and stored. These approaches can involve constructing a centralized memory or database to store a wide variety of optical aberration characteristics and clinical characteristics associated with one or more optics, where there is a substantial amount of heterogeneity across the characteristics.

Further, these techniques can advantageously provide a database system that simplifies the complications of analyzing data from different wavefront systems, different aberrometer devices and aberrometer software versions, different clinical studies and different measurement conditions. A centralized database system can be used effectively in a clinical research setting, which can be a medical center, a college, or a research department in a company, or in other diagnosis or treatment facilities.

Database maintenance can be performed to enhance the availability of data. Input of data can be done either with database scripts or standalone applications. With Open DataBase Connectivity (ODBC), Java DataBase Connectivity (JDBC), or similar protocols, automatic reports can be generated periodically with the use of commercially available reporting tools. In addition, correlations can be generated on demand and data gathering for research can be performed with standalone applications or database scripts. The centralized database system can be used effectively in a clinical research setting, which can be a medical center, a college, or a research department in a firm. Pupil sizes, pupil images, spot patterns, topographies, Zernike coefficients, WaveScan® measurements, and clinical data such as visual acuity, manifest refraction, contrast sensitivity, questionnaire results, or the like can be standardized in a common database, thus facilitating data integrity, consistency, availability, and manageability. Databases can be constructed to store raw wavefront data from a variety of sensors.

In one aspect, the present invention provides a computer system for processing optical data. The computer system can include a memory and a processor communicatively coupled with the memory. The processor can be configured to access optical data stored by the memory. The optical data can include wavefront aberration data of a plurality of optics, and the wavefront aberration data of at least one of the optics can include a first format data. The processor can be configured to modify the first format data to a second format data. The wavefront data can further include a third format data, and the processor can be configured to modify the third format data to second format data. The wavefront data can further include second format data. The wavefront data can include a plurality of additional format data different than first and second format data, and the processor can be configured to modify at least one of the additional format data to second format data. At least one of the optics can be selected from a group consisting of an eye, a cornea, a lens, and an optical system. The first format data can include a Malacara coordinate system format data. The second format data can include an Optical Society of America (OSA) standard format data. In some aspects, the optical data can further include a first optical coefficient indicating a first optical characteristic, and the processor can be further configured to modify the first optical characteristic according to a second optical coefficient different from the first optical coefficient.

In another aspect, the present invention provides a computer apparatus for processing optical data. The computer apparatus can include a memory configured to store optical data. The optical data can include wavefront aberration data of a plurality of optics. A first optical characteristic of at least one of the optics can include a first format data. The computer apparatus can also include a modification module that includes at least one of (i) a transformation module configured to transform the first format data to a second format data and (ii) a conversion module configured to convert the first format data to a second format data.

The computer apparatus can include a correlation module configured to correlate the first optical characteristic with a second optical characteristic. The apparatus can further include a reporting module configured to provide statistical analysis of the optical data. Similarly, the reporting module can be communicatively coupled with the memory via at least one of an Open DataBase Connectivity (ODBC) and a Java DataBase Connectivity (JDBC). The computer apparatus can include an administration module configured to maintain a copy of the memory. The computer apparatus can also include a data pulling component configured to cache optical data from the memory. What is more, the computer apparatus can include an inputting module configured to input optical data into the memory. In some instances, the memory can include a database.

In still another aspect, the present invention provides a computer program product for modifying a first format wavefront aberration data to a second format wavefront aberration data. The computer program product can include code for retrieving from a memory optical data comprising an optical characteristic of one or more optics, wherein an optical characteristic of at least some of the one or more optics can include the first format wavefront aberration data. The product can also include code for modifying the first format wavefront aberration data to the second format wavefront aberration data. Similarly, the product can include a computer-readable medium for storing the codes.

The present invention also provides a computer-implemented method for processing optical data. The method can include receiving an instruction to retrieve from a memory optical data comprising an optical characteristic of one or more of optics, wherein the optical characteristic of at least some of the one or more optics includes a first format wavefront aberration data. The method can also include receiving an instruction to modify the first format wavefront aberration data to a second format wavefront aberration data.

In one aspect, the present invention provides a method for processing optical data. The method can include retrieving from a memory optical data comprising an optical characteristic of one or more of optics, wherein the optical characteristic of at least some of the one or more optics comprising wavefront aberration data in a plurality of different formats. The method can also include modifying at least some of the wavefront aberration data in the plurality of different formats to a common format.

In another aspect, the present invention provides a method for processing optical data. The method can include accessing optical data for a first optic, wherein the first optic optical data includes wavefront aberration data in a first data format. The method can also include accessing optical data for a second optic, wherein the second optic optical data includes wavefront aberration data in a second data format. Further, the method can include modifying the second optic optical data to a first data format, and comparing clinical data associated with the first and second optics using the first and second optic optical data in the first data format. Similarly, the method can include accessing optical data from a third optic, wherein the third optic optical data comprising wavefront data in a plurality of different data formats. The method can also include modifying the third optic optical data to the first data format based on the comparison of the clinical data.

In still another aspect, the present invention provides a method for determining an optical treatment shape. The method can include accessing optical data for a first optic, wherein the first optic optical data can include wavefront aberration data in a first data format. The method can also include accessing optical data for a second optic, wherein the second optic optical data can include (i) wavefront aberration data in a second data format, and (ii) clinical data. The method can also include modifying the second optic wavefront aberration data to the first data format, and determining an optical treatment shape for the first optic based on the second optic clinical data and a comparison between the first and second optic wavefront aberration data in the first data format. The first format data can include a Malacara coordinate system format data. The second format data can include an Optical Society of America (OSA) standard format data.

DETAILED DESCRIPTION OF THE INVENTION

The present invention can be readily adapted for use with existing laser systems, wavefront measurement systems, and other optical measurement devices. While the systems, software, and methods of the present invention are described primarily in the context of a laser eye surgery system, it should be understood the present invention may be adapted for use in alternative eye treatment procedures and systems such as spectacle lenses, intraocular lenses, contact lenses, corneal ring implants, collagenous corneal tissue thermal remodeling, and the like.

Figure 1:
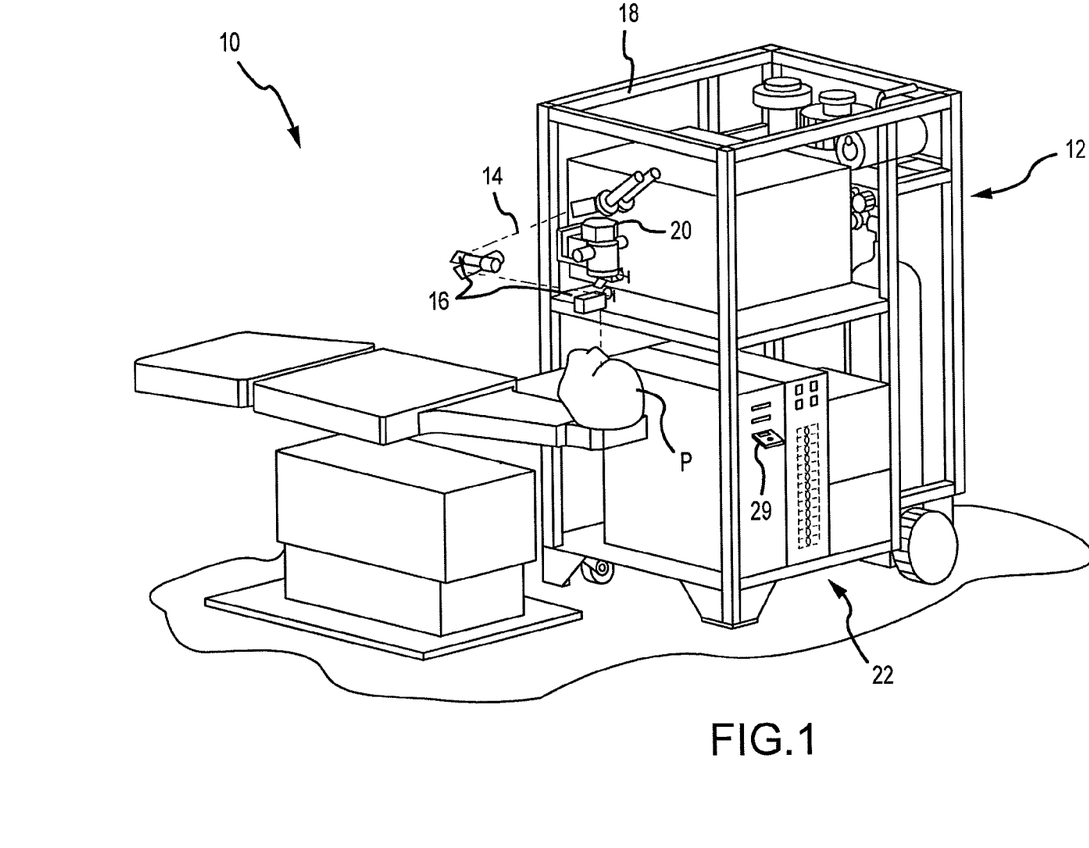
FIG. 1 illustrates a laser ablation system according to an embodiment of the present invention.

Turning now to the drawings, FIG. 1 illustrates a laser eye surgery system 10 of the present invention, including a laser 12 that produces a laser beam 14. Laser 12 is optically coupled to laser delivery optics 16, which directs laser beam 14 to an eye E of patient P. A delivery optics support structure (not shown here for clarity) extends from a frame 18 supporting laser 12. A microscope 20 is mounted on the delivery optics support structure, the microscope often being used to image a cornea of eye E.

Laser 12 generally comprises an excimer laser, ideally comprising an argon-fluorine laser producing pulses of laser light having a wavelength of approximately 193 nm. Laser 12 will preferably be designed to provide a feedback stabilized fluence at the patient's eye, delivered via delivery optics 16. The present invention may also be useful with alternative sources of ultraviolet or infrared radiation, particularly those adapted to controllably ablate the corneal tissue without causing significant damage to adjacent and/or underlying tissues of the eye. Such sources include, but are not limited to, solid state lasers and other devices which can generate energy in the ultraviolet wavelength between about 185 and 205 nm and/or those which utilize frequency-multiplying techniques. Hence, although an excimer laser is the illustrative source of an ablating beam, other lasers may be used in the present invention.

Laser system 10 will generally include a computer or programmable processor 22. Processor 22 may comprise (or interface with) a conventional PC system including the standard user interface devices such as a keyboard, a display monitor, and the like. Processor 22 will typically include an input device such as a magnetic or optical disk drive, an internet connection, or the like. Such input devices will often be used to download a computer executable code from a tangible storage media 29 embodying any of the methods of the present invention. Tangible storage media 29 may take the form of a floppy disk, an optical disk, a data tape, a volatile or non-volatile memory, RAM, or the like, and the processor 22 will include the memory boards and other standard components of modern computer systems for storing and executing this code. Tangible storage media 29 may optionally embody wavefront sensor data, wavefront gradients, a wavefront elevation map, a treatment map, a corneal elevation map, and/or an ablation table. While tangible storage media 29 will often be used directly in cooperation with a input device of processor 22, the storage media may also be remotely operatively coupled with processor by means of network connections such as the internet, and by wireless methods such as infrared, Bluetooth, or the like.

Laser 12 and delivery optics 16 will generally direct laser beam 14 to the eye of patient P under the direction of a computer 22. Computer 22 will often selectively adjust laser beam 14 to expose portions of the cornea to the pulses of laser energy so as to effect a predetermined sculpting of the cornea and alter the refractive characteristics of the eye. In many embodiments, both laser beam 14 and the laser delivery optical system 16 will be under computer control of processor 22 to effect the desired laser sculpting process, with the processor effecting (and optionally modifying) the pattern of laser pulses. The pattern of pulses may by summarized in machine readable data of tangible storage media 29 in the form of a treatment table, and the treatment table may be adjusted according to feedback input into processor 22 from an automated image analysis system in response to feedback data provided from an ablation monitoring system feedback system. Optionally, the feedback may be manually entered into the processor by a system operator. Such feedback might be provided by integrating the wavefront measurement system described below with the laser treatment system 10, and processor 22 may continue and/or terminate a sculpting treatment in response to the feedback, and may optionally also modify the planned sculpting based at least in part on the feedback. Measurement systems are further described in U.S. Pat. No. 6,315,413, the full disclosure of which is incorporated herein by reference.

Laser beam 14 may be adjusted to produce the desired sculpting using a variety of alternative mechanisms. The laser beam 14 may be selectively limited using one or more variable apertures. An exemplary variable aperture system having a variable iris and a variable width slit is described in U.S. Pat. No. 5,713,892, the full disclosure of which is incorporated herein by reference. The laser beam may also be tailored by varying the size and offset of the laser spot from an axis of the eye, as described in U.S. Pat. Nos. 5,683,379, 6,203,539, and 6,331,177, the full disclosures of which are incorporated herein by reference.

Still further alternatives are possible, including scanning of the laser beam over the surface of the eye and controlling the number of pulses and/or dwell time at each location, as described, for example, by U.S. Pat. No. 4,665,913, the full disclosure of which is incorporated herein by reference; using masks in the optical path of laser beam 14 which ablate to vary the profile of the beam incident on the cornea, as described in U.S. Pat. No. 5,807,379, the full disclosure of which is incorporated herein by reference; hybrid profile-scanning systems in which a variable size beam (typically controlled by a variable width slit and/or variable diameter iris diaphragm) is scanned across the cornea; or the like. The computer programs and control methodology for these laser pattern tailoring techniques are well described in the patent literature.

Additional components and subsystems may be included with laser system 10, as should be understood by those of skill in the art. For example, spatial and/or temporal integrators may be included to control the distribution of energy within the laser beam, as described in U.S. Pat. No. 5,646,791, the full disclosure of which is incorporated herein by reference. Ablation effluent evacuators/filters, aspirators, and other ancillary components of the laser surgery system are known in the art. Further details of suitable systems for performing a laser ablation procedure can be found in commonly assigned U.S. Pat. Nos. 4,665,913, 4,669,466, 4,732,148, 4,770,172, 4,773,414, 5,207,668, 5,108,388, 5,219,343, 5,646,791 and 5,163,934, the complete disclosures of which are incorporated herein by reference. Suitable systems also include commercially available refractive laser systems such as those manufactured and/or sold by Alcon, Bausch & Lomb, Nidek, WaveLight, LaserSight, Schwind, Zeiss-Meditec, and the like. Basis data can be further characterized for particular lasers or operating conditions, by taking into account localized environmental variables such as temperature, humidity, airflow, and aspiration.

Figure 2:
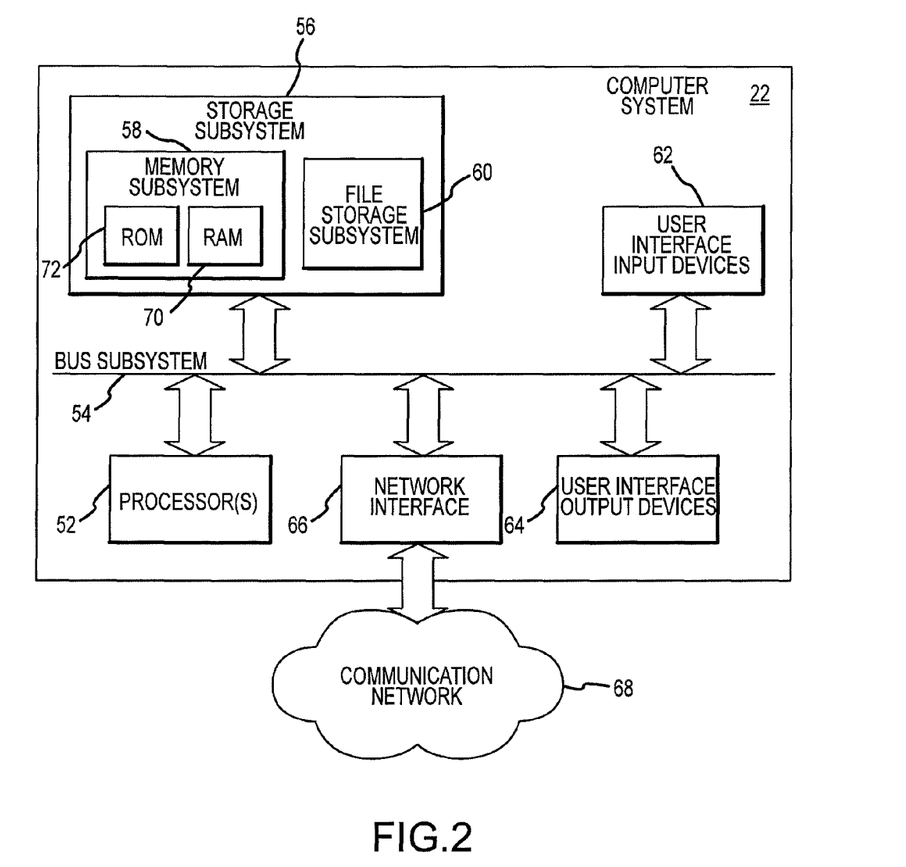
FIG. 2 illustrates a simplified computer system according to an embodiment of the present invention.

FIG. 2 is a simplified block diagram of an exemplary computer system 22 that may be used by the laser surgical system 10 of the present invention. Computer system 22 typically includes at least one processor 52 which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices, such as the wavefront measurement system 30.

User interface input devices 62 may include a keyboard, pointing devices such as a mouse, trackball, touch pad, or graphics tablet, a scanner, foot pedals, a joystick, a touchscreen incorporated into the display, audio input devices such as voice recognition systems, microphones, and other types of input devices. User input devices 62 will often be used to download a computer executable code from a tangible storage media 29 embodying any of the methods of the present invention. In general, use of the term "input device" is intended to include a variety of conventional and proprietary devices and ways to input information into computer system 22.

User interface output devices 64 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from computer system 22 to a user.

Storage subsystem 56 can store the basic programming and data constructs that provide the functionality of the various embodiments of the present invention. For example, a database and modules implementing the functionality of the methods of the present invention, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files, and may include tangible storage media 29 (FIG. 1) which may optionally embody wavefront sensor data, wavefront gradients, a wavefront elevation map, a treatment map, and/or an ablation table. File storage subsystem 60 may include a hard disk drive, a floppy disk drive along with associated removable media, a Compact Digital Read Only Memory (CD-ROM) drive, an optical drive, DVD, CD-R, CD-RW, solid-state removable memory, and/or other removable media cartridges or disks. One or more of the drives may be located at remote locations on other connected computers at other sites coupled to computer system 22. The modules implementing the functionality of the present invention may be stored by file storage subsystem 60.

Bus subsystem 54 provides a mechanism for letting the various components and subsystems of computer system 22 communicate with each other as intended. The various subsystems and components of computer system 22 need not be at the same physical location but may be distributed at various locations within a distributed network. Although bus subsystem 54 is shown schematically as a single bus, alternate embodiments of the bus subsystem may utilize multiple busses.

Computer system 22 itself can be of varying types including a personal computer, a portable computer, a workstation, a computer terminal, a network computer, a control system in a wavefront measurement system or laser surgical system, a mainframe, or any other data processing system. Due to the ever-changing nature of computers and networks, the description of computer system 22 depicted in FIG. 2 is intended only as a specific example for purposes of illustrating one embodiment of the present invention. Many other configurations of computer system 22 are possible having more or less components than the computer system depicted in FIG. 2.

Figure 3:
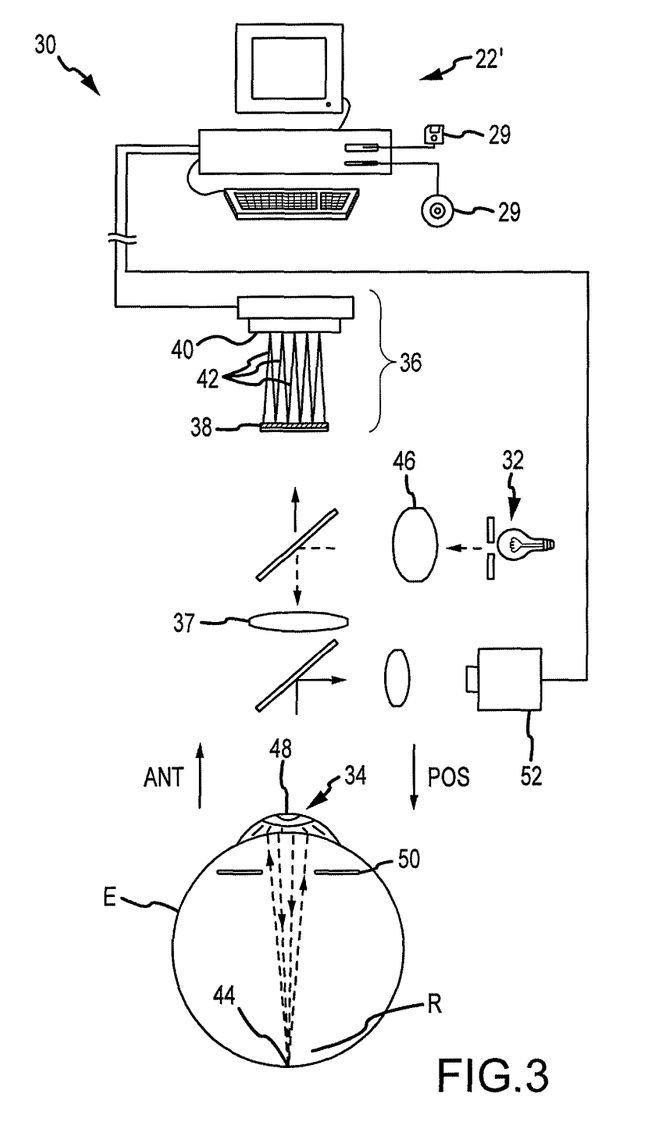
FIG. 3 illustrates a wavefront measurement system according to an embodiment of the present invention.

Referring now to FIG. 3, one embodiment of a wavefront measurement system 30 is schematically illustrated in simplified form. In very general terms, wavefront measurement system 30 is configured to sense local slopes of a gradient map exiting the patient's eye. Devices based on the Hartmann-Shack principle generally include a lenslet array to sample the gradient map uniformly over an aperture, which is typically the exit pupil of the eye. Thereafter, the local slopes of the gradient map are analyzed so as to reconstruct the wavefront surface or map.

More specifically, one wavefront measurement system 30 includes an image source 32, such as a laser, which projects a source image through optical tissues 34 of eye E so as to form an image 44 upon a surface of retina R. The image from retina R is transmitted by the optical system of the eye (e.g., optical tissues 34) and imaged onto a wavefront sensor 36 by system optics 37. The wavefront sensor 36 communicates signals to a computer system 22' for measurement of the optical errors in the optical tissues 34 and/or determination of an optical tissue ablation treatment program. Computer 22' may include the same or similar hardware as the computer system 22 illustrated in FIGS. 1 and 2. Computer system 22' may be in communication with computer system 22 that directs the laser surgery system 10, or some or all of the components of computer system 22, 22' of the wavefront measurement system 30 and laser surgery system 10 may be combined or separate. If desired, data from wavefront sensor 36 may be transmitted to a laser computer system 22 via tangible media 29, via an I/O port, via an networking connection 66 such as an intranet or the Internet, or the like.

Wavefront sensor 36 generally comprises a lenslet array 38 and an image sensor 40. As the image from retina R is transmitted through optical tissues 34 and imaged onto a surface of image sensor 40 and an image of the eye pupil P is similarly imaged onto a surface of lenslet array 38, the lenslet array separates the transmitted image into an array of beamlets 42, and (in combination with other optical components of the system) images the separated beamlets on the surface of sensor 40. Sensor 40 typically comprises a charged couple device or "CCD," and senses the characteristics of these individual beamlets, which can be used to determine the characteristics of an associated region of optical tissues 34. In particular, where image 44 comprises a point or small spot of light, a location of the transmitted spot as imaged by a beamlet can directly indicate a local gradient of the associated region of optical tissue.

Eye E generally defines an anterior orientation ANT and a posterior orientation POS. Image source 32 generally projects an image in a posterior orientation through optical tissues 34 onto retina R as indicated in FIG. 3. Optical tissues 34 again transmit image 44 from the retina anteriorly toward wavefront sensor 36. Image 44 actually formed on retina R may be distorted by any imperfections in the eye's optical system when the image source is originally transmitted by optical tissues 34. Optionally, image source projection optics 46 may be configured or adapted to decrease any distortion of image 44.

In some embodiments, image source optics 46 may decrease lower order optical errors by compensating for spherical and/or cylindrical errors of optical tissues 34. Higher order optical errors of the optical tissues may also be compensated through the use of an adaptive optic element, such as a deformable mirror (described below). Use of an image source 32 selected to define a point or small spot at image 44 upon retina R may facilitate the analysis of the data provided by wavefront sensor 36. Distortion of image 44 may be limited by transmitting a source image through a central region 48 of optical tissues 34 which is smaller than a pupil 50, as the central portion of the pupil may be less prone to optical errors than the peripheral portion. Regardless of the particular image source structure, it will be generally be beneficial to have a well-defined and accurately formed image 44 on retina R.

In one embodiment, the wavefront data may be stored in a computer readable medium 29 or a memory of the wavefront sensor system 30 in two separate arrays containing the x and y wavefront gradient values obtained from image spot analysis of the Hartmann-Shack sensor images, plus the x and y pupil center offsets from the nominal center of the Hartmann-Shack lenslet array, as measured by the pupil camera 51 (FIG. 3) image. Such information contains all the available information on the wavefront error of the eye and is sufficient to reconstruct the wavefront or any portion of it. In such embodiments, there is no need to reprocess the Hartmann-Shack image more than once, and the data space required to store the gradient array is not large. For example, to accommodate an image of a pupil with an 8 mm diameter, an array of a 20×20 size (i.e., 400 elements) is often sufficient. As can be appreciated, in other embodiments, the wavefront data may be stored in a memory of the wavefront sensor system in a single array or multiple arrays.

While the methods of the present invention will generally be described with reference to sensing of an image 44, it should be understood that a series of wavefront sensor data readings may be taken. For example, a time series of wavefront data readings may help to provide a more accurate overall determination of the ocular tissue aberrations. As the ocular tissues can vary in shape over a brief period of time, a plurality of temporally separated wavefront sensor measurements can avoid relying on a single snapshot of the optical characteristics as the basis for a refractive correcting procedure. Still further alternatives are also available, including taking wavefront sensor data of the eye with the eye in differing configurations, positions, and/or orientations. For example, a patient will often help maintain alignment of the eye with wavefront measurement system 30 by focusing on a fixation target, as described in U.S. Pat. No. 6,004,313, the full disclosure of which is incorporated herein by reference. By varying a position of the fixation target as described in that reference, optical characteristics of the eye may be determined while the eye accommodates or adapts to image a field of view at a varying distance and/or angles.

The location of the optical axis of the eye may be verified by reference to the data provided from a pupil camera 52. In the exemplary embodiment, a pupil camera 52 images pupil 50 so as to determine a position of the pupil for registration of the wavefront sensor data relative to the optical tissues.

Figure 3A:
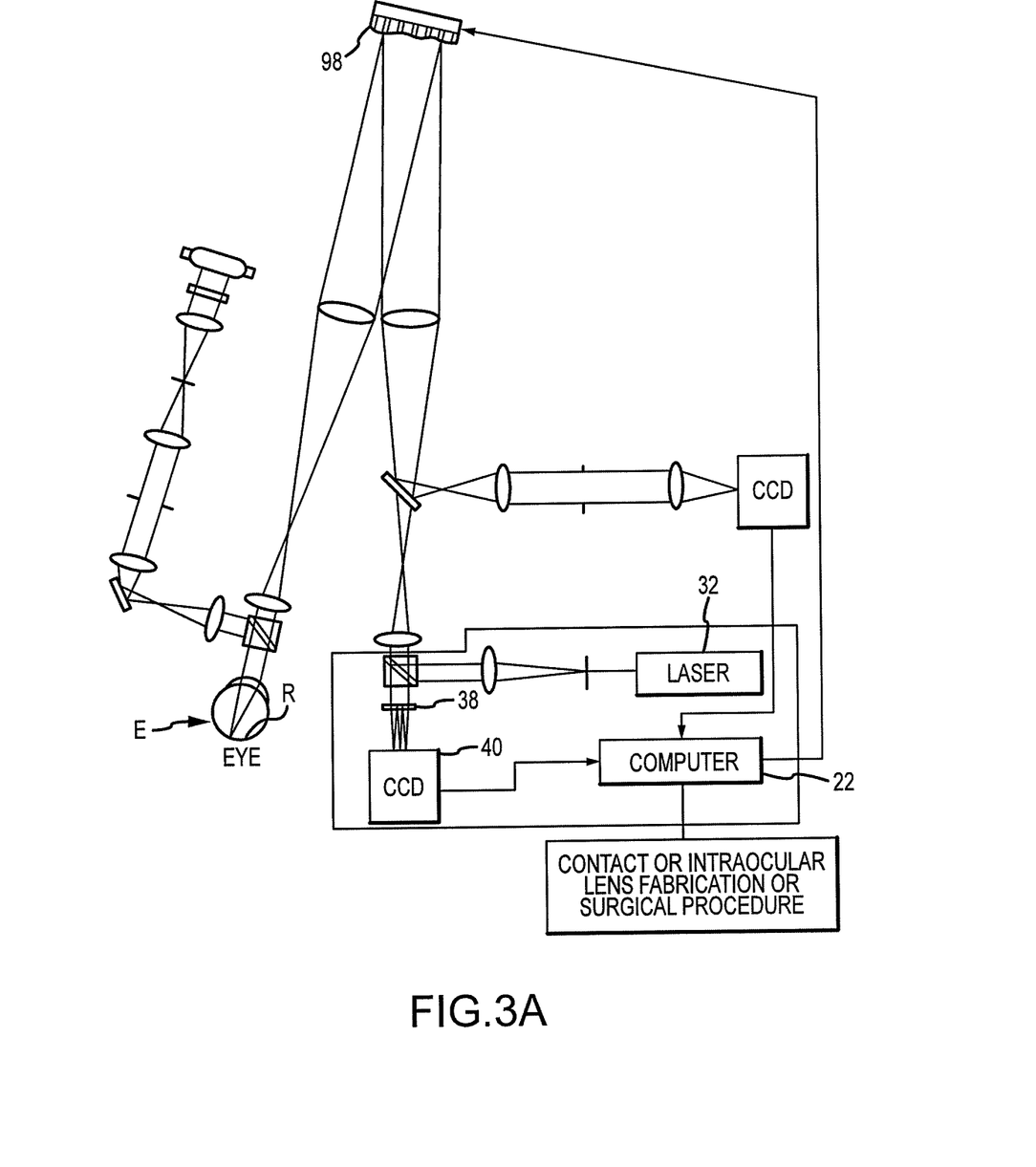
FIG. 3A illustrates another wavefront measurement system according to an embodiment of the present invention.

An alternative embodiment of a wavefront measurement system is illustrated in FIG. 3A. The major components of the system of FIG. 3A are similar to those of FIG. 3. Additionally, FIG. 3A includes an adaptive optical element 53 in the form of a deformable mirror. The source image is reflected from deformable mirror 98 during transmission to retina R, and the deformable mirror is also along the optical path used to form the transmitted image between retina R and imaging sensor 40. Deformable mirror 98 can be controllably deformed by computer system 22 to limit distortion of the image formed on the retina or of subsequent images formed of the images formed on the retina, and may enhance the accuracy of the resultant wavefront data. The structure and use of the system of FIG. 3A are more fully described in U.S. Pat. No. 6,095,651, the full disclosure of which is incorporated herein by reference.

The components of an embodiment of a wavefront measurement system for measuring the eye and ablations may comprise elements of a VISX WaveScan®, available from VISX, INCORPORATED of Santa Clara, Calif. One embodiment includes a WaveScan® with a deformable mirror as described above. An alternate embodiment of a wavefront measuring system is described in U.S. Pat. No. 6,271,915, the full disclosure of which is incorporated herein by reference. It is appreciated that any wavefront aberrometer could be employed for use with the present invention.

Often, databases at different institutions will vary widely in the way information is modeled, represented, and retrieved. Similarly, databases within the same institution can include data recorded in different formats, such as older and newer data formats associated with different time periods. When analyzing such information, complications can arise due to the presence of different types of data formats, data storage and processing systems, data collection software applications, clinical study or evaluation approaches, and measurement conditions. Accordingly, new approaches are needed to perform information analysis, especially when data from different measurement systems are selected for the analysis, and there is a lack of homogeneity across system and data formats. Relatedly, it may be desirable for a single computer system to retrieve or use information, for example, from databases of different institutions. In such cases, the processing steps in the computer system may need to be customized differently for the information associated with each institution.

Ocular aberration data is one type of data that is collected and stored in a wide variety of systems and formats. To effectively utilize this information, it can be helpful to either transfer legacy data from an old system to a new system, or to use a new system to interface with data contained in a legacy system. These approaches can be referred to as data mapping, data transfer, or legacy data conversion, and may involve the modification of information in a first data format or model to a second data format or model which can be further processed.

There are a variety of ocular aberration measurement systems. For example, wavefront aberration systems, including the WaveScan® (VISX Incorporated, Santa Clara, Calif.), can provide information regarding refractive errors or aberrations of the eye, and vision treatments can be planned based on the measured aberrations. The first official version of the WaveScan® measurement system provides a data output known as WavePrint® 1.0, which uses a Malacara coordinate system to characterize the optical data. The Malacara coordinate system differs from the Optical Society of America (OSA) standard in certain respects. The exported Zernike coefficients of the WavePrint® 1.0 data are raw data, which can be multiplied by the pupil radius in microns in order to obtain the desired Zernike coefficients in microns, which is the OSA standard format. Furthermore, the coefficients of the WavePrint® 1.0 data correspond to un-normalized Zernike polynomials, which again differ from the OSA standard.

WaveScan® version 2.5 provides a different data format than that provided by earlier software versions. WaveScan® versions 2.5 and later may use normalized Zernike Polynomials with the OSA standard, and the reported coefficients correspond to the real optical path difference (OPD) in microns. There is a considerable amount of optical aberration data that is recorded in earlier versions such as the WavePrint® 1.0 data format. It is often desirable to analyze such legacy data in conjunction with data that is available in more recent data formats or standards, or by using newer computer system and software applications that may not be configured for the legacy data.

Figure 4:
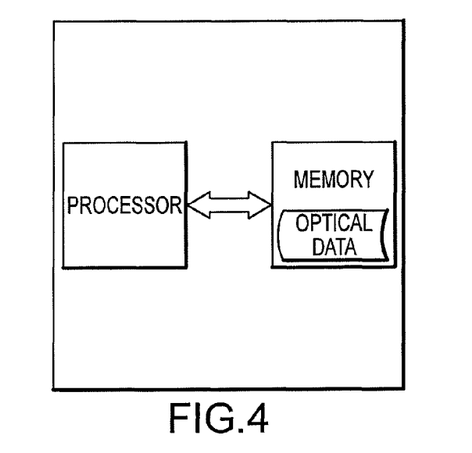
FIG. 4 illustrates a computer system according to an embodiment of the present invention.

As shown in FIG. 4, one embodiment of the present invention includes a computer system having a processor and a memory communicatively coupled with the processor. The memory can be configured to store optical data accessible by the processor. Often, the optical data will include optical aberration characteristics or clinical characteristics of one or more optics. Further, characteristics of at least some of the one or more optics can include a first format data. The processor of the computer system may be configured to modify the first format data to a second format data. According to some embodiments of the present invention, a computer system may include one or more processors.

I. Optics

Optics of the present invention can include eyes, corneas, lenses, and other optical systems.

II. Optical Data

Optical data can include optical characteristics such as optical aberration characteristics or clinical characteristics of one or more optics. Optical aberration characteristics can include wavefront aberration data, as well as non-wavefront aberration data such as topography data. For example, in the case where the optic is a human eye, the wavefront aberration data typically includes Zernike coefficients and pupil size, as well as the pupil images and spot patterns. Alternatively, wavefront aberration data can include non-Zernike data, such as Fourier-based data, in which case, the gradient field (x- and y-gradients) can be stored. Wavefront data may be generated from WaveScan® or other wavefront devices. In situations where the optic is a human cornea, topography data can include a full pupil image as well as elevation files in a ring-type coordinate. Another example of an optical aberration characteristic is root-mean-square (RMS), which can be classified as either wavefront or non-wavefront aberration data.

Clinical characteristics may include, but are not limited to, pre-operative visual acuity measurements, post-operative visual acuity measurements, uncorrected visual acuity (UCVA), best spectacle corrected visual acuity (BSCVA), demographic data (e.g., age, sex, and ethnic group), manifest refraction, cycloplegic refraction, pachemetry, pupilometry, blur range, residual accommodation, certain diagnoses, laboratory results, medication orders, drug allergies, surgery related parameters, and the like. The clinical characteristics can be helpful for generating reports useful for Investigational Device Exemption (IDE) submission and Premarketing Approval (PMA) applications. They are also helpful for doing on-demand correlations.

III. Data Format

Medical and clinical information such as optical data may exist in a variety of data formats, and it is often desirable to convert data from a first formatted data such as an original or legacy formatted data to a second formatted data such as a standard formatted data. For example, optical data can include optical coefficients, based on various parameters such as optical path difference or tissue depth. In some embodiments, the present invention will provide for the processing of optical data that comprises a first optical coefficient indicating a first optical characteristic, such that the first optical characteristic is modified according to a second optical coefficient that is different from the first optical coefficient. In some embodiments, optical data comprising an OPD-based coefficient indicating wavefront aberration data can be modified according to a non-OPD based coefficient. Examples of non-OPD based coefficients include peak-to-valley (PV) and root-mean-square (RMS) after algorithm fitting.

Optical data can be processed according to any of a variety of modification algorithms, such as conversion algorithms and coordinate transformation algorithms. As noted above, the exported Zernike coefficients of the WavePrint® 1.0 data are raw data and can be converted by multiplying by the pupil radius in microns in order to obtain the desired Zernike coefficients in microns. In some circumstances, conversion algorithms can convert unnormalized formatted data to normalized formatted data. For example, unnormalized Zernike coefficients can be converted to normalized Zernike coefficients using the following conversion factors:

if m=0, then divide by $\sqrt{(n+1)}$ if m≠0, then divide by $\sqrt{2(n+1)}$ where m is the azimuthal frequency, and n is the radial degree or Zernike order.

Relatedly, it may be desirable to transform some Zernike coefficients to Malacara formatted Zernike coefficients or to OSA formatted Zernike coefficients.

The Malacara coordinate system, which is discussed in D. Malacara, "Optical Shop Testing," 2nd Ed., (John Wiley & Sons, Inc. New York, 1992), uses the following non-conventional polar coordinate transformation:

$x=r^* \sin(\text{theta})$ $y=r^* \cos(\text{theta})$

The Optical Society of America (OSA) standard, which is discussed by L. N. Thibos, R. A. Applegate, J. T. Schwiegerling, and R. Webb, in "Standards for reporting the optical aberrations of eyes," J. Refract. Surg., vol. 18, S652-S660 (2002), uses the following more conventional polar coordinate transformation:

$x=r^*\cos(\text{theta})$ $y=r^*\sin(\text{theta})$

With regard to data consistency issues, the approaches of the present invention can improve consistent data representation of surfaces, regardless of which version of software is used (e.g., WavePrint®), which clinical study is analyzed, or which wavefront device is used. A universal data scheme can provide consistency.

The systems and method described herein may also beneficially include or be combined with ongoing Nomogram work in the ophthalmological field.

In some embodiments, the present invention provides a method for processing optical data such as wavefront data. This method can include accessing optical data for a first optic, such as wavefront aberration data for a first eye in a standard data format. The method can also include accessing optical data for a second optic, such as wavefront aberration for a second eye in a legacy data format. In such methods, the second optic legacy formatted data can be converted to the standard data format. The method often involves comparing clinical data associated with the first and second optics using the first and second optical data in the standard data format.

In other embodiments, the present invention provides a method for determining an optical treatment shape. This method can include accessing optical data for a first optic, such as wavefront aberration data for a first eye in a standard data format. The method can also include accessing optical data for a second optic, such as wavefront aberration for a second eye in a legacy data format. In such methods, the second optic legacy formatted data can be converted to the standard data format. The method often involves determining an optical treatment shape for the first optic based on the second optic clinical data and a comparison between the first and second optic optical data in the standard data format.

In one embodiment of the present invention, a database can be implemented with the following schema. Two sets of database tables can be implemented; one for staging and the other for production. The set of staging tables are automatically created from the data loading with Java codes. During the staging period, all of the raw data are stored in the staging table. The table structure can be modified on the fly according to the input data format. It is possible that no filtering, verification, or integration of data is implemented at this stage. Once this step is completed, a special table that contains MetaData of the production table is updated so as to steer the loading of staging data into production tables. The production tables contain all the final data that fulfills the data integrity, consistency, availability, and manageability requirements. Data format conversion may be done during pre-processing.

A. Database Schema

Figure 5:
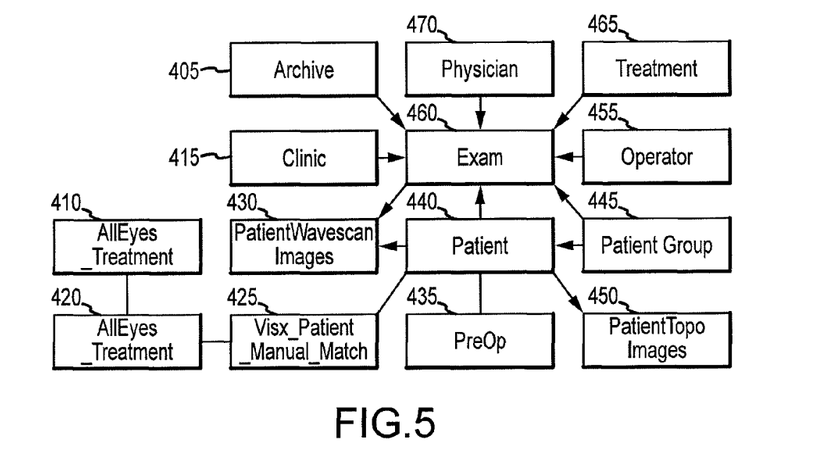
FIG. 5 illustrates a production database schema according to an embodiment of the present invention.

FIG. 5 illustrates the production database schema according to one embodiment of the present invention. Clinical characteristics, or clinical optometric examination data, such as pre-operative and post-operative visual acuity measurements, data collected during the surgery, and demographic data, can be stored in the AllEyes table 420. The Exam table 460 can contain optical aberration characteristics such as wavefront maps represented either by means of Zernike coefficients or gradient fields. Data for inputting into the Exam table 460 can be generated, for example, by performing individual WaveScan® examinations.

In FIG. 5, a line connecting two entities (e.g., tables) without an arrow denotes a one-to-one relationship. A line with an arrow represents a one-to-many relationship, where the arrow points from the "one" toward the "many." For example, one physician 470 can be associated with many exams 460. Archive table 405 can contain data that is archived from an Exam table 460. AllEyes_Treatment table 410 can contain data from a clinical examination of AllEyes table 420 taken during the surgery date which can be a specific calendar day. Clinic table 415 can contain information identifying or associated with the clinic that generated the Exam table 460. AllEyes table 420 can contain clinical optometric examination data taken from, for example, pre-operation and post-operation optometric examinations. VISX_Patient_Manual_Match table 425 can match patient by patient and eye by eye between AllEyes table 420 and Patient table 440.

In some cases, the first name and last name of a patient are entered into a WaveScane device and are contained in the Patient table 440, yet they may not match their counterparts in the AllEyes table 420. The Visx_Patient_Manual_Match table 425 can pull the two sets of names together to reach a one-to-one relation. PatientWaveScanImages table 430 can contain images from a WaveScan® device. For example, PatientWaveScanimages table 430 can contain four Hartmann-Shack spot patterns and one pupil image for each exam. PreOp table 435 can contain pre-operation parameters that may be needed by a WaveScan® device, such as manifest refraction and keratometry values that are duplicates in AllEyes table 420. Patient table 440 can contain a patient's last name, first name, and initials, which can be entered by a WaveScan® operator.

Patient_Group table 445 can contain patient group or groups of patients in different studies or cohorts. Patient-TopoImages table 450 can contain pre-operative and post-operative topography data, including the topographic surface image and the related ring data. Operator Table 455 can contain information about the operator that performs a WaveScan® exam. Exam table 460 can contain information for each WaveScan® exam, such as Zernike coefficients, pre-compensation of sphere and cylinder, and pupil sizes. Treatment table 465 can contain information about treatment tables that are generated from a WaveScan® device. Physician table 470 can contain information about the physician who performs the surgery. The shaded boxes in FIG. 5 (reference numbers 410, 420, 430, 440, 450, 460, and 470) can represent entities that contain "real" data that can be searched or extracted.

B. Manual Matching

During database loading, it may be useful to perform a manual matching of names. For example, the AllEyes table 420 may contain the name Joe Smith, as correctly entered by the operator into an Excel spreadsheet. However, during the WaveScan® examination, the name may have been inadvertently entered incorrectly by the operator as Smith Joe, effectively switching the first and last names. Hence, it may be difficult to complete automatic production loading for records that have such name reversals. In order to complete such automatic loading, it may be necessary to manually enter both sets of names into the Visx_Patient_Manual_Match table 425 so that the Java code can automatically process these records. Once a one-to-one relation between the two sets of names is obtained, it is possible to complete the production loading with the automatic process. With such a centralized database, it is foreseeable that there could be two different individuals sharing the same name "Joe Smith" in the database. In order to distinguish the two individuals named "Joe Smith," it may be helpful to use a special column "Research Study" to appear in each production table. Furthermore, it is also possible to use the Site ID, or the clinic to make sure such name duplication is eliminated. In some embodiments, Research Study and Site ID will be contained in each of the tables.

IV. Data Input/Loading

Optical data are typically input to computer applications to analyze the data for research, diagnostic, or treatment purposes. Data input can include importing optical data, having optical aberration characteristics and clinical characteristics, into a database system or memory. For example, from the data flow, it is natural for a clinical representative to do data loading with specific tools as the raw data usually is generated in a clinical department. Ideally, the input tools will be simple and easy to operate. Input can be accomplished at a variety of levels. For example, input may be performed on a per patient basis, with regard to questionnaires, data on binocular performance, quality of life, and the like. Input may also be performed on a per eye basis, with regard to high order aberrations (HOA), healing, and the like. Similarly, input may be performed on a per study basis. Database contents can be reconstructed on demand using Zernike, Fourier, or other methods for comparison purposes and statistical analysis.

Database loading applications can have object-oriented packages to manipulate common tasks. These common tasks include database connection, disk caching, memory caching, database object exchange and manipulation.

Such database loading approaches may also enable data integrity, consistency, availability, and manageability. With regard to data integrity issues, for example, these approaches may ensure that there is no duplication among records. Duplicate records can be an issue when performing a simple add-up or data join of different versions of WaveScan® exports for the same set of patients for measurements taken from different time periods. Data verification can also be used to accomplish such tasks.

Examples of data input or loading approaches include database scripts, Windows-based standalone applications, and Web-based applications.

A. Database Scripts

The data-loading component can include database scripts such as Structural Query Language (SQL) scripts. For SQL scripts, different database vendors have slightly different syntax but the difference is quite limited.

If SQL script loading approach is selected, all the data connection information (user name, password) can be stored in the script. The input file name and some other information, such as software version, study ID, etc, can be run as command-line arguments.

B. Windows-Based Applications

The data-loading component can also include Windows-based applications. Such applications can be programmed in any of a variety of computer languages, including the programming language of C/C++.

Figure 6:
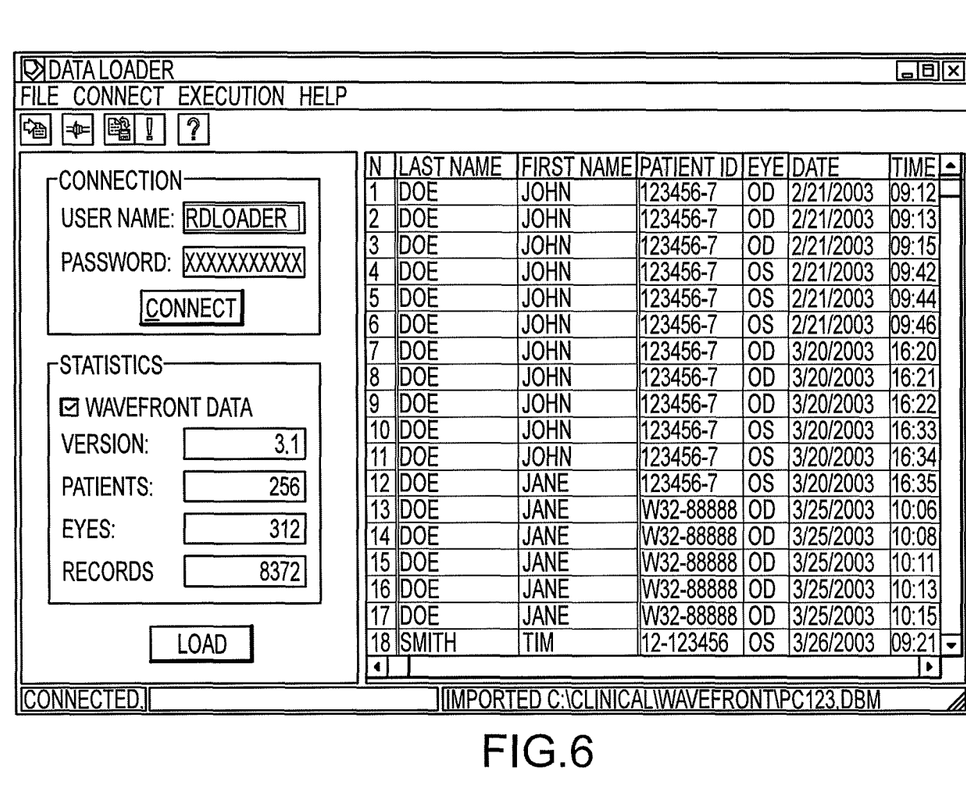
FIG. 6 illustrates a screen shot of a data loader application according to an embodiment of the present invention.

FIG. 6 shows a screen shot of an exemplary Windows-based Data Loader application, which can be developed by programs such as Borland C++ Builder. In one embodiment, the Data Loader can include two primary panels. Here, a first panel includes login and the statistics of the loaded data. A second panel shows the loaded data in a StringGrid table for reviewing purpose. Once it is determined that there is no error during the loading, the user can click the Commit button to make the database commit to the changes. This can serve as a verification function. If, on the other hand, an error occurs, the program can perform an automatic rollback operation upon program termination or other user-driven action.

Figure 8:
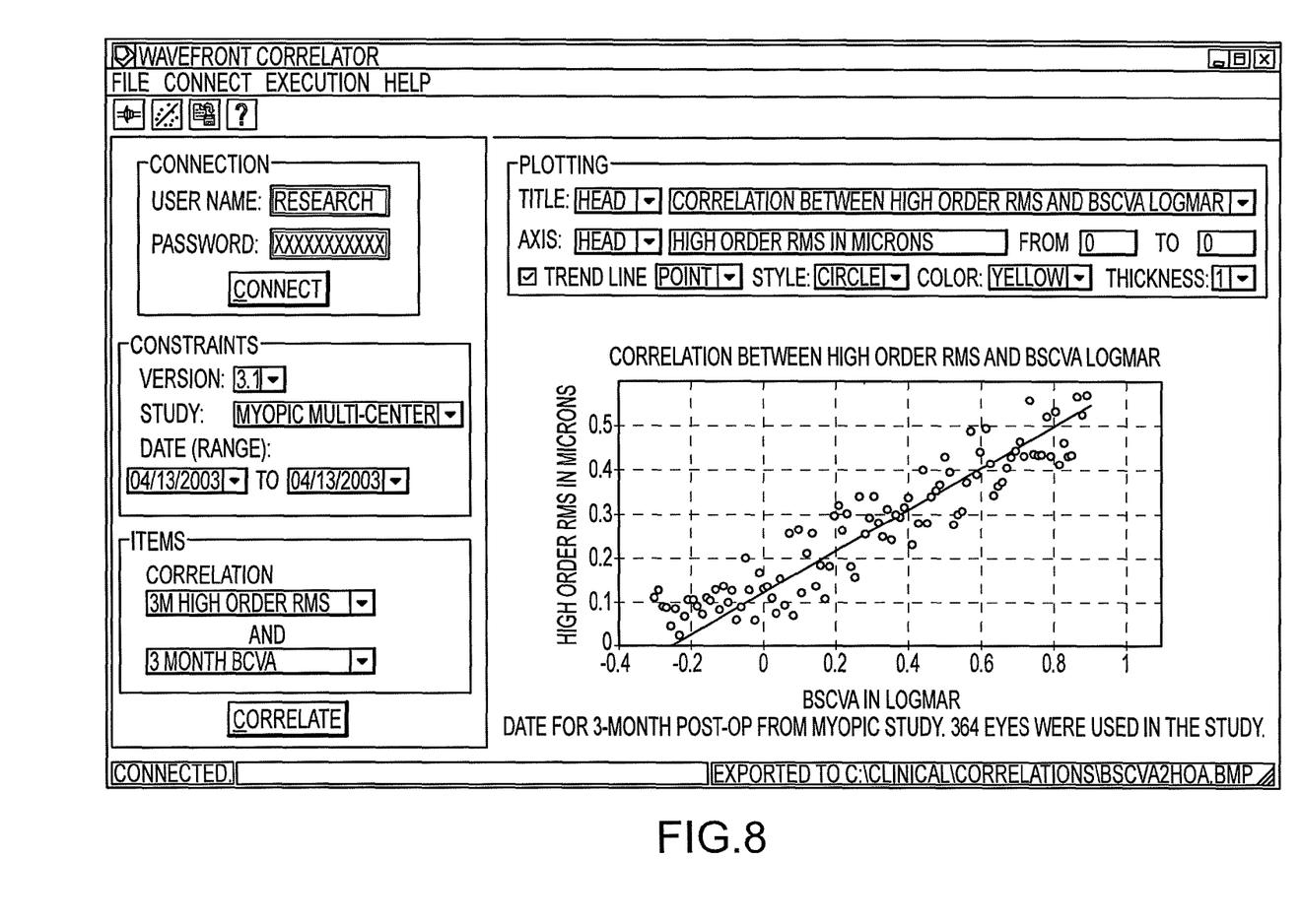
FIG. 8 illustrates a screen shot of a wavefront correlator application according to an embodiment of the present invention.

For Windows-based applications, C++ Builder is a useful Integrated Development Environment (IDE) for constructing a loader, correlator, or other module as shown in FIG. 8.

C. Web-Based Applications

Figure 7:
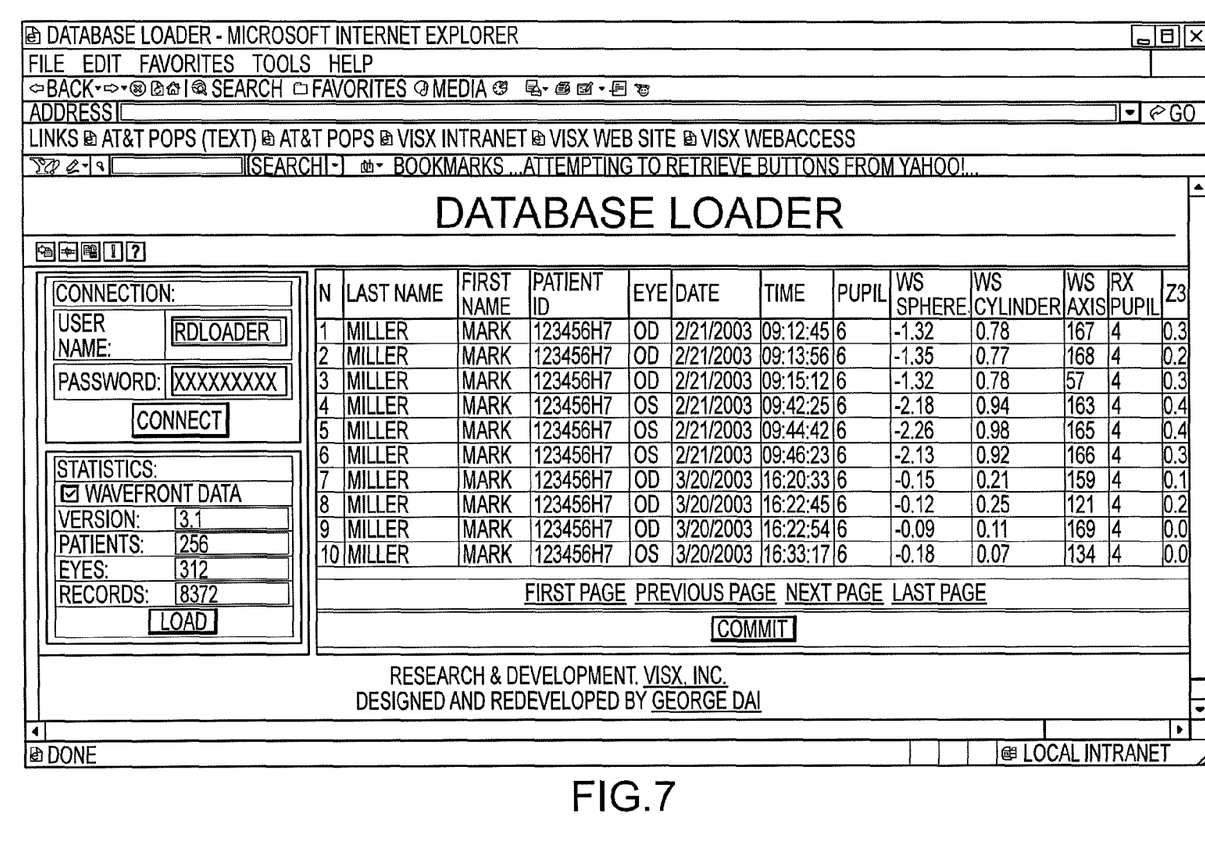
FIG. 7 illustrates a screen shot of a database loader application according to an embodiment of the present invention.

Web-based applications can operate with platform independence. The same software can be run in any computer platform, such as Windows, McIntosh, HP Unix, Sun Solaris, DEC Ultrix, IBM AIX, Linux, and the like. FIG. 7 shows a screen shot of an exemplary Web-based Database Loader application. The design of a web-based application may be very similar to the design of a Windows-based application. For Web-based applications, JavaBeans, JavaServlet, CGI with Perl, JavaScript, and VB Script can be used. Data format modification typically occurs prior to input into permanent memory such as hard disk, floppy disk, CD-R, flash memory, tapes, and the like. Data format modification may also occur prior to or subsequent to temporary storage or buffering.

D. Connectivity

In general terms, database connectivity refers to the protocol, or set of rules, between a physical database, such as a database platform, and a database application, such as a program. Often, the connectivity is defined by a user, manufacturer, or other body to standardize the communication. Graphical user interface (GUI) tools such as Integrated Development Environment (IDE) tool, C++ Builder, Open DataBase Connectivity (ODBC), Active database object (ADO), or Borland Database Engine (BDE) can be used for the database connectivity, for example, between the different modules of FIG. 9. For web-based applications, Java programming language can be used with Java DataBase Connectivity (JDBC) protocol as a database connectivity protocol between, for example, a database engine and a java or a java-related program such as JavaBeans or Java Servlets. Apart from Java, other languages can also be used such as JavaScript and VB Script. For windows-based applications, ODBC is often used. Perl programming language can be used to realize Common Gateway Interface (CGI). When using Perl, a Perl module of DBI/DBD with ODBC libraries from specific database vendors can be used. With regard to database scripts, there may be no connectivity protocol as these scripts are often run directly on the database platform.

V. Memory

Memory, for example a database engine, can be a commercially available database product, such as Oracle Corporation's Oracle, IBM Corporation's DB2 and Informix, Microsoft Corporation's SQL Server and Access, and Sybase Inc.'s Sybase. In one embodiment, the computer system of the present invention includes an SQLServer database.

VI. Data Output

A centralized database or memory can be useful for many data output purposes. For example, a database can support research activities such as (1) automatic reporting; (2) on-demand correlation; and (3) data pulling for research. These activities can be performed at a variety of levels. For example, querying may be performed on a per patient basis, with regard to questionnaires, data on binocular performance, quality of life, and the like. Querying may also be performed on a per eye basis, with regard to high order aberrations (HOA), healing, and the like. Similarly, querying may be performed on a per study basis. Database contents can be reconstructed on demand using Zernike, Fourier, or other methods for comparison purposes and statistical analysis.

A. Reporting

For database reporting, there are a number of commercially available reporting tools, such as Crystal Report, Brio, and Actuate. Any of a variety of protocols can be used for the connectivity between the database and the reporting tool. For example, in one embodiment of the present invention, ODBC is used as a connectivity protocol. With ODBC, JDBC, or similar protocols, automatic reports can be generated periodically with the use of commercially available reporting tools.

Automatic reporting can include statistical reports that include the number of patients, number of eyes, and number of wavefront scans that have been done over a period of time. It can also include some simple calculations such as average high order (HO) root-mean-square (RMS) error over a period of time or for a whole study. Calculation of such items can be implemented by means of database built-in functions or triggers. Database built-in functions can be functionalities that require user interaction. For example, a user can run sqrt(4), and the computer returns a value of 2. Triggers can be user-defined functionalities, and are database action driven. For example, a user can define a trigger to allow a reporting when the database happens to have a −12D patient. When the database contains such a database point, either by database loading or update, the database can generate such a report. Therefore, no other external programming tools may be needed except for the commercially available reporting tool. It is possible to add a feature in the reporting process so that one or more copies of the reports can be sent automatically to one or more recipients via automatic email.

B. Correlation

On-demand correlation can be implemented by SQL scripts, Windows-based standalone applications, or web-based applications. Correlation plots may be required when submitting applications to an agency such as the FDA for an IDE study or PMA approval. In other cases, similar plots or graphical outputs may be required for marketing purpose, or for generating figures for physicians in presentations. FIG. 8 shows a screen mockup for a Windows-based Wavefront Correlator application.

Similar to the Database Loader, the on-demand correlator can also be implemented with web-based applications. For the plotting portion, image manipulation tools or modules can be used to generate exportable images. For instance, when CGI is used, Perl modules such as ImageMagic can be used for generating required graphs. When Java-based technology is used, such as JavaBeans or JavaServlet, more image manipulation and processing packages may be available as possible choices.

On-demand correlation can be used for generating correlations between two data series whenever needed, which is relatively simple and easy. For example, FIG. 8 shows a correlation between a High Order RMS first optical characteristic and a BSCVA LogMAR second optical characteristic. It will be appreciated that any two sets of parameters can be correlated.

C. Data Pulling

For the data pulling for research component, both Windows-based standalone applications and web-based applications can be implemented, although SQL script can also be used for the same purpose. No matter which approach is used, a common portion of the component, the database connection, caching (disk caching and memory caching), and object exchange and manipulation can be implemented as one or more object-oriented packages so that different applications can share the same code for reusability and productivity. Code sharing also increases manageability.

On the other hand, data pulling for research can be very specific to the application and there might be a set of applications rather than a single application. Therefore, Java-based technology can be used. In this case, the database connectivity portion can be implemented as JavaBeans or Servlets and different applications can share the same code for accessing the database.

VII. Database Management/Administration

The database management component involves management of the data, and can include data input, data output, database update, account and role management, database redundancy, automatic emergency reporting, security considerations, database backup and recovery, database version upgrade, and database tuning. In one embodiment of the present invention, this component can be managed by an information technology (IT) department.

Database update can be done by loading tools. A database administrator may be discouraged to use the super user role to do data updating or deleting. In order to keep the database online at all times, the following two set of schemes can be used: (1) database redundancy; (2) automatic emergency reporting.

A. Redundancy

For database redundancy, two identical database systems can be constructed in two separate computers. Both computers can run the same database version from the same vendor. The two databases can be synchronized with database built-in synchronization tools or external replication tools. A database view can then be created so that it can point to either system. When one system is down because of hardware or software failure, only one SQL command may be required to switch the view to point to the other database system. This can help ensure the availability of the database at all times. Database maintenance can be performed to secure the availability of data at any time and under any circumstances.

With regard to data availability issues, these approaches can ensure that the data on-request function is available at any time. These issues can be addressed with online and/or offline backup of the memory or database. Offline database backup once a week may be preferred.

Database administration tasks can address the availability and security of information. However, if the database is not accessible through Internet, the level of security may not necessarily need to be high. In order for the database to be available all the time, it is possible to have two copies of the database, pointed by a single database view; When one database is not available due to software or hardware failure, the database view can be changed to point to the other physical database through just a single SQL command. Synchronization between the two copies of the database can be performed according to the frequency of the database update (input). As for the database backup, offline backup once a week may be sufficient for most situations, although online backup may be more often used by transactional databases. Offline backup may be more economical for a data warehouse than for a transactional database.

B. Emergency Reporting

For automatic emergency reporting, one simple application can be constructed with periodic database connection attempts. A database automatic emergency reporting tool can have an automatic connection attempt, between a database engine and an external report-generating module, with frequency between one minute and one hour, for example, depending on how critical it is to have the database available. A simple application can be written in any possible language, and an email component can be included so that when the application detects a database malfunction, it can send an emergency email to the appropriate person. Another possible way to accomplish automatic emergency reporting is for the application to send a short message to the cellular phone of the operator or other recipient.

C. Security

Security considerations such as strict role control can be effected, for example, by limiting and distinguishing operators who run data input from operators who perform data correlation.

VIII. Total System

Figure 9:
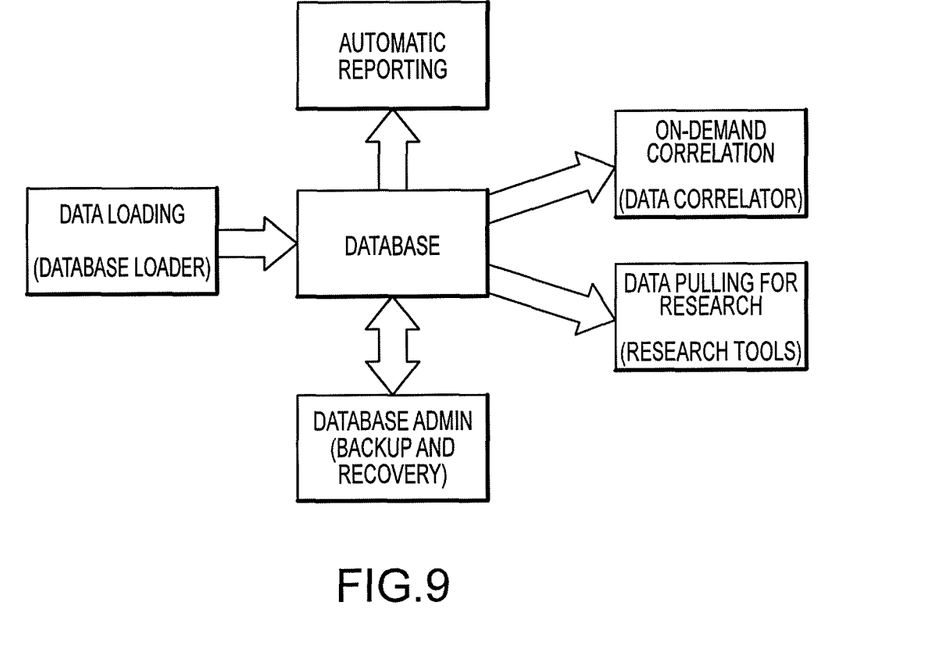
FIG. 9 illustrates an exemplary system according to an embodiment of the present invention.

As shown in FIG. 9, an exemplary database system can include the following components: a commercial database engine, a data loading component, an automatic reporting component, a database administration component, an on-demand correlation component, and a data pulling for research component.

In one embodiment of the present invention, a database system can be constructed to centralize available optical data, including optical aberration characteristics and clinical characteristics.

It can be appreciated by one of skill in the art that all parameters, variables, factors, algorithms, and the like can be incorporated into method steps or system modules. While the specific embodiments have been described in some detail, by way of example and for clarity of understanding, a variety of adaptations, changes, and modifications will be obvious to those of skill in the art. Although the invention has been described with specific reference to a wavefront system using lenslets, other suitable wavefront systems that measure angles of light passing through the eye may be employed. For example, systems using the principles of ray tracing aberrometry, tscherning aberrometry, and dynamic skiascopy may be used with the current invention. The above systems are available from TRACEY Technologies of Bellaire, Tex., Wavelight of Erlangen, Germany, and Nidek, Inc. of Fremont, Calif., respectively. The invention may also be practiced with a spatially resolved refractometer as described in U.S. Pat. Nos. 6,099,125; 6,000,800; and 5,258,791, the full disclosures of which are incorporated herein by reference. Treatments that may benefit from the invention include intraocular lenses, contact lenses, spectacles and other surgical methods in addition to refractive laser corneal surgery. Therefore, the scope of the present invention is limited solely by the appended claims.

What is claimed is:

1. A computer system for processing optical data, the computer system comprising:
   a memory; and
   a processor communicatively coupled with the memory, the processor configured to access optical data stored by the memory, the optical data comprising wavefront aberration data of a plurality of optics, the wavefront aberration data of at least one of the optics comprising a first format data, and the processor configured to modify the first format data to a second format data,
   wherein the first format data comprises a Hartmann-Shack spot pattern and a pupil image,
   wherein the first format data comprises a first optical coefficient indicating a first optical characteristic, and the processor is configured to modify the first optical characteristic according to a second optical coefficient different from the first optical coefficient,
   wherein the computer system is configured to receive operator information about an operator that performs a wavefront examination and physician information about a physician that performs a surgery, and
   wherein the computer system is configured to determine an optical treatment shape based on the operator information, the physician information, and the second format data.

2. The computer system of claim 1, wherein the wavefront data further comprises a third format data, the processor configured to modify the third format data to second format data.

3. The computer system of claim 1, wherein the wavefront data further comprises second format data.

4. The computer system of claim 1, wherein the wavefront data comprises a plurality of additional format data different than first and second format data, the processor configured to modify at least one of the additional format data to second format data.

5. The computer system of claim 1, wherein at least one of the optics is selected from a group consisting of an eye, a cornea, a lens, and an optical system.

6. The computer system of claim 1, wherein the first format data comprises a Malacara coordinate system format data.

7. The computer system of claim 1, wherein the second format data comprises an Optical Society of America (OSA) standard format data.

8. The computer system of claim 1, wherein the memory comprises a database.

9. The computer system of claim 1, wherein the second format data comprises a non-wavefront data.

10. The computer system of claim 1, wherein the first optical coefficient comprises an OPD-based coefficient, and the second optical coefficient comprises a non-OPD based coefficient.

11. A computer apparatus for processing optical data, the computer apparatus comprising:
   a memory configured to store optical data, the optical data comprising wavefront aberration data of a plurality of optics, a first optical characteristic of at least one of the optics comprising a first format data; and
   a modification module comprising at least one of (i) a transformation module configured to transform the first format data to a second format data and (ii) a conversion module configured to convert the first format data to a second format data,
   wherein the first format data comprises a first optical coefficient indicating a first optical characteristic, and the modification module is configured to modify the first optical characteristic according to a second optical coefficient different from the first optical coefficient,
   wherein the computer apparatus is configured to receive operator information about an operator that performs a wavefront examination, to receive physician information about a physician that performs a surgery, and to determine an optical treatment shape based on the operator information, the physician information, and the second format data, and
   wherein the first format data comprises a peak-to-valley coefficient.

12. The computer apparatus of claim 11, further comprising a correlation module configured to correlate the first optical characteristic with a second optical characteristic.

13. The computer apparatus of claim 11, further comprising a reporting module configured to provide statistical analysis of the optical data.

14. The computer apparatus of claim 13, wherein the reporting module is communicatively coupled with the memory via at least one of an Open DataBase Connectivity (ODBC) and a Java DataBase Connectivity (JDBC).

15. The computer apparatus of claim 11, further comprising an administration module configured to maintain a copy of the memory.

16. The computer apparatus of claim 11, further comprising a data pulling component configured to cache optical data from the memory.

17. The computer apparatus of claim 11, further comprising an inputting module configured to input optical data into the memory.

18. The computer apparatus of claim 11, wherein the memory comprises a database.

19. A method for determining an optical treatment shape, the method comprising:
   accessing optical data for a first optic, the first optic optical data comprising wavefront aberration data in a first data format;
   accessing optical data for a second optic, the second optic optical data comprising (i) wavefront aberration data in a second data format, and (ii) clinical data;
   accessing operator information about an operator that performs a wavefront examination;
   accessing physician information about a physician that performs a surgery;
   modifying the second optic wavefront aberration data to the first data format; and
   determining an optical treatment shape for the first optic based on the operator information, the physician information, the second optic clinical data, and a comparison between the first and second optic wavefront aberration data in the first data format,
   wherein the second optic optical data comprises a second optical coefficient indicating a second optical characteristic, and the modifying step includes modifying the second optical characteristic according to a first optical coefficient different from the second optical coefficient.

20. The method of claim 19, wherein the first format data comprises a Malacara coordinate system format data.

21. The method of claim 19, wherein the second format data comprises an Optical Society of America (OSA) standard format data.

* * * * *